United States Patent
Pirhonen et al.

(10) Patent No.: US 6,926,903 B2
(45) Date of Patent: Aug. 9, 2005

(54) RESORBABLE POLYMER COMPOSITION, IMPLANT AND METHOD OF MAKING IMPLANT

(75) Inventors: Eija Pirhonen, Tampere (FI); Jan Nieuwenhuis, Gorinchem (NL); Auvo Kaikkonen, Tampere (FI); Tuomo Nieminen, Tampere (FI); Franz Weber, Singen (DE)

(73) Assignee: Inion Ltd., Tampere (FI)

( * ) Notice: Subject to any disclaimer, the term of this patent is extended or adjusted under 35 U.S.C. 154(b) by 60 days.

(21) Appl. No.: 10/006,800

(22) Filed: Dec. 4, 2001

(65) Prior Publication Data

US 2003/0104029 A1 Jun. 5, 2003

(51) Int. Cl.[7] .......................... A61K 2/02; A61K 47/30
(52) U.S. Cl. .................... 424/426; 514/772.3; 523/114; 523/115
(58) Field of Search ...................... 424/426; 514/772.3; 523/114, 115

(56) References Cited

U.S. PATENT DOCUMENTS

| | | | |
|---|---|---|---|
| 5,077,049 A | 12/1991 | Dunn et al. ................ 424/426 |
| 5,378,472 A | 1/1995 | Muzzarelli .................. 424/445 |
| 5,725,491 A | 3/1998 | Tipton et al. ................. 602/43 |
| 5,939,323 A | * 8/1999 | Valentini et al. ............ 435/395 |
| 6,162,537 A | * 12/2000 | Martin et al. ............... 428/373 |
| 6,245,345 B1 | 6/2001 | Swanbom et al. .......... 424/402 |
| 6,261,583 B1 | 7/2001 | Dunn et al. ................. 424/422 |

FOREIGN PATENT DOCUMENTS

WO WO 96/39134 A1 12/1996
WO WO 02/00137 A1 1/2002

OTHER PUBLICATIONS

Muzzarelli et al., "Osteoconduction exerted by methylpyrrolidinone chitosan used in dental surgery," *Biomaterials*, 14(1):39–43 (1993).

* cited by examiner

Primary Examiner—Carlos A. Azpuru
(74) Attorney, Agent, or Firm—Banner & Witcoff, Ltd.

(57) ABSTRACT

Novel polymer compositions that are useful in the manufacture of medical implants, implants having osteogenic properties and methods of making said implants are disclosed. Polymer compositions comprise a base material including a polymer matrix of resorbable polymer(s) or copolymer(s), and N-methyl-2-pyrrolidone (NMP), wherein NMP is present in an amount imparting osteogenic properties for the composition.

23 Claims, 1 Drawing Sheet

RESORBABLE POLYMER COMPOSITION, IMPLANT AND METHOD OF MAKING IMPLANT

FIELD OF THE INVENTION

The present invention relates to novel polymer compositions that are useful in the manufacture of medical implants. More particularly, embodiments of the invention relate to polymer compositions having osteogenic properties. The polymer compositions are biodegradable or bioresorbable and they can be fashioned into medical implants for implantation in the body. Implants having osteogenic properties and methods of making said implants are also disclosed.

BACKGROUND OF THE INVENTION

The healing process of bone is a complicated cascade of events. Rapid and diverse events are activated by a fracture or osteotomy of a bone in order to limit the loss of blood and initiate cellular migration resulting in repair. Current concepts suggest that these cellular events are controlled to a large part by growth factors, low-molecular-weight glycoproteins, inducing migration, proliferation and differentiation of an appropriate subset of cells in the site of the fracture.

Despite of the amount of known details the bone healing as a whole is still a poorly understood process. Based on this lacking information and experimental data research has revealed several methods to enhance bone growth, such as mechanical stimulation, electromagnetic fields, low-intensity ultrasound, osteoconductive materials, for instance hydroxyapatite, tricalcium phosphate, bioactive glass etc., and osteoinductive materials, such as growth factors.

Osteoinduction is a process where any substance, stimulation etc. starts or enhances a cellular response resulting in a bone formation process. Growth factors are a wide group of molecules known to possess this effect. According to the current knowledge, bone morphogenetic proteins (BMP) are the only growth factors known to induce bone formation heterotopically by inducing undifferentiated mesenchymal cells to differentiate into osteoblasts. Consequently, several BMPs are shown to boost the bone healing process when supplementary doses are given.

For example, U.S. Pat. No. 5,725,491 discloses a biodegradable film dressing as a delivery system of various therapeutic agents, such as BMPs. The therapeutic agent is delivered from the film dressing in a certain and controlled release rate. However, BMPs are produced by genetic engineering, which is still rather expensive. Also, delivery of a correct dose of BMPs is difficult and presents great challenges for the future.

Known materials, methods and implants are expensive and exploitation of such materials, methods and implants is constrained.

BRIEF DESCRIPTIONS OF THE INVENTION

An object of the present invention is to provide novel resorbable polymer compositions having osteogenic properties so as to alleviate the above disadvantages. Another object is to provide novel resorbable implants having osteogenic properties. A further object is to provide methods of making resorbable implants having osteogenic properties.

These objects are achieved by providing resorbable polymer compositions, resorbable implants and methods of making resorbable implants comprising a base material including a polymer matrix of resorbable polymer(s) or copolymer(s) and N-methyl-2-pyrrolidone (NMP).

According to one embodiment of the invention, the polymer matrix comprises Polylactide/Polyglycolide/Trimethylene carbonate copolymer (PLA/PGA/TMC) with a composition of 80/10/10.

According to another embodiment of the invention, the polymer matrix comprises Poly D, L-lactide/Poly L-lactide/Trimethylene carbonate copolymer (PLDLA/PLA/TMC) with a composition of 55/40/5.

According to a third embodiment of the invention, the polymer matrix comprises 80 wt-% P(L/DL)LA (70/30) and 20 wt-% PLLA/TMC (70/30).

According to a fourth embodiment of the invention, the implant is a membrane.

According to one embodiment of the method of the invention, the method comprises the steps of selecting polymer(s) or copolymer(s) of a polymer matrix of the implant, mixing said polymer(s) or copolymer(s) to form the polymer matrix, forming the implant from said polymer matrix, and adding NMP to the implant in an amount imparting osteogenic properties for said implant.

According to another embodiment of the method of the invention, the method comprises the steps of selecting polymer(s) or copolymer(s) of a polymer matrix of the implant, adding NMP to the polymer matrix in an amount imparting osteogenic properties for the implant, and forming the implant from the mixture of said polymer matrix and NMP.

An advantage of polymer compositions, implants and methods of the invention is that substantially inexpensive products are achieved as compared with known solutions enhancing bone healing.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figures 1A, 1B, 1C:
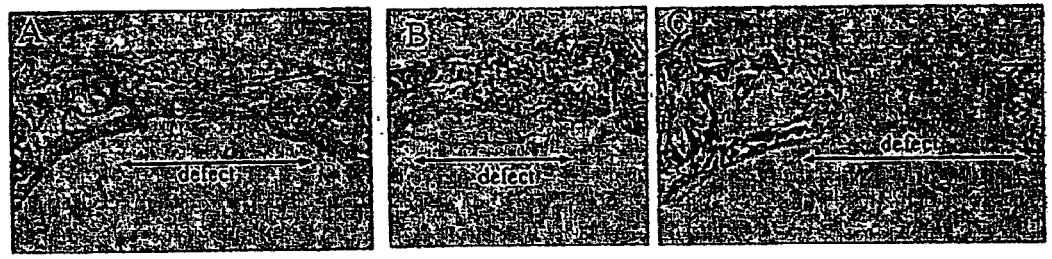
FIG. 1a is a microscope view of a histological section of a defect created in rabbit calvarial bone where said defect is covered by a (PLA/PGA/TMC) 80/10/10 membrane treated with NMP as described in example 1.
FIG. 1b is a second microscope view of a histological section of a defect created in rabbit calvarial bone where said defect is covered by an OsseoQuest membrane.
FIG. 1c is a third microscope view of a histological section of a defect created in rabbit calvarial bone where said defect is without any membrane.

The present invention relates to a combination of N-methyl-2-pyrrolidone (NMP) and resorbable polymers or copolymers. The invention is based on the unexpected realization that by combining a resorbable matrix material and NMP in a certain ratio, an implant having osteogenic properties is achieved. The implant thus induces bone growth due to the osteogenic properties of the polymer composition and enhances bone healing after osteotomies and bone fractures.

The implant forms include, but are not limited to, membranes, films, plates, mesh plates, screws, taps or other formed pieces.

The implant can be prepared for example of polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides (like cellulose, starch, dextran, chitin, chitosan, etc.), modified proteins (like collagen, casein, fibrin, etc.) and their copolymers, terpolymers or combinations or mixtures or polymer blends thereof. Polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D, L-lactide-co-caprolactone) polytrimethylenecarbonate, poly (L-lactide-co-trimethylenecarbonate), poly(D,L-lactide-co-trimethylenecarbonate), polydioxanone and copolymers, terpolymers and polymer blends thereof are highly preferred polymers.

EXAMPLE 1

Polylactide/Polyglycolide/Trimethylene carbonate copolymer (PLA/PGA/TMC), with a composition of 80/10/10, granulates were compression moulded to form a film with a thickness of 0.2 mm. Used compression temperature was 180° C. and pressure 130 bar. From the film 10 rectangular pieces were cut, each with a width of 20 mm.

The weight of the individual film pieces were measured with balance with an accuracy of 1 mg. The film pieces were then immersed individually into NMP for 30 seconds. After immersion the film pieces were air dried for 20 minutes and the weight of the pieces was measured again.

The weight of the film pieces before and after immersion into NMP are shown in table 1. The average amount of NMP diffused into polymeric film was 44.19%.

TABLE 1

The weight of the film pieces before and after immersion into NMP

| Weight before immersion into NMP (mg) | Weight after immersion into NMP (mg) | NMP content (mg) | Polymer content (%) | NMP content (%) |
| --- | --- | --- | --- | --- |
| 56.41 | 98.95  | 42.54 | 57.01 | 42.99 |
| 67.29 | 115.40 | 48.11 | 58.31 | 41.69 |
| 60.22 | 105.40 | 45.18 | 57.13 | 42.87 |
| 59.77 | 101.35 | 41.58 | 58.97 | 41.03 |
| 56.48 | 110.25 | 53.77 | 51.23 | 48.77 |
| 66.62 | 118.52 | 51.9  | 56.21 | 43.79 |
| 64.16 | 114.42 | 50.26 | 56.07 | 43.93 |
| 62.58 | 114.24 | 51.66 | 54.78 | 45.22 |
| 56.29 | 104.32 | 48.03 | 53.96 | 46.04 |
| 62.53 | 114.82 | 52.29 | 54.46 | 45.54 |

GTR membranes produced with the method described here in were used in a comparable rabbit study disclosed in example 2.

EXAMPLE 2

This rabbit study shows the osteogenetic effect of PLA/PGA/TMC and PLDLA/PLA/TMC membranes when treated with NMP. The details of the tested membranes can be found in the following table 2.

TABLE 2

Materials and codes of example 2

| Code | Materials |
| --- | --- |
| E1M-11 NMP | PLA/PGA/TMC (80/10/10), treated with NMP (see EXAMPLE 1) |
| E1M-11 | PLA/PGA/TMC (80/10/10) |
| E1M-3 NMP | PLDLA/PLA/TMC (55/40/5), treated with NMP (as in EXAMPLE 1) |
| E1M-3 | PLDLA/PLA/TMC (55/40/5) |
| OsseoQuest | PLA/PGA/TMC supplier W. L. GORE & Associates, Inc. |
| E1M-11 with holes | PLA/PGA/TMC (80/10/10), with holes manufactured using Laser |
| TMC/PLA | PLA/TMC (70/30) |

The study design included eight rabbits with four 6-mm artificial craniotomy defects each. The defects were treated with biodegradable membranes and a commercial biodegradable OsseoQuest membrane as shown in table 2. Controls treated without any membranes were included, too. The matrixes of the resorbable membranes are also presented in table 2.

The rabbits were sacrificed 4 weeks after the operation and the calvarial bone excised. Thorough histological analysis was performed in order to assess the degree and type of bone regeneration.

FIGS. 1a to 1c illustrate examples of some histological sections from the middle of the defect. It is clearly evident that the bone formed during the 4-week repair phase is more a cancellous bone than a cortical bone. A cellular interaction with the membrane was not observed.

Figure 2:
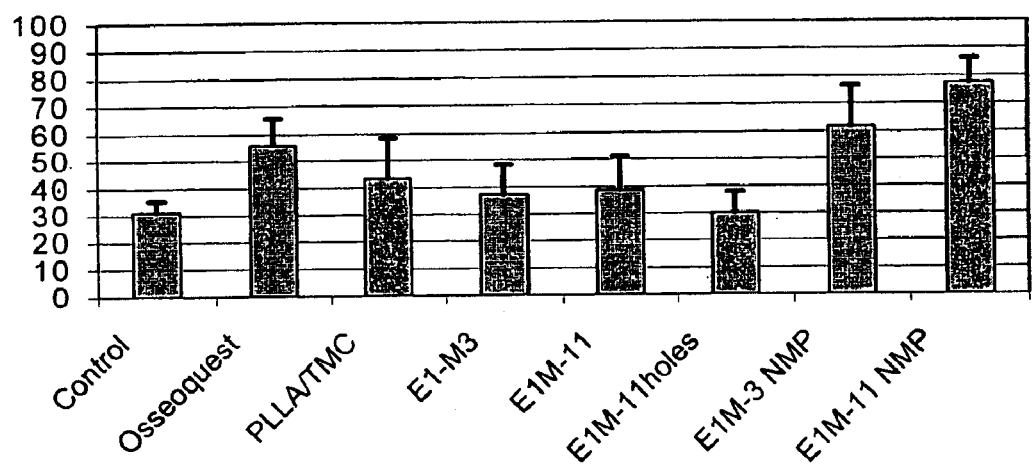
FIG. 2 is a graph showing repair of rabbit calvarial bone defects.

FIG. 2 shows the percentage of a full-thickness repair of rabbit calvarial bone defects. The middle sections of the defects, 6 mm in diameter in the calvarial bone were evaluated. The percentage of repair was determined by pixel number of the defect filled with bone×100/pixel number of the defect area. The different membranes are specified by name. 'Control' means the defect without the application of a membrane.

Evaluation of the level of a full-thickness repair of the bone defect revealed that the use of membranes improved bone healing. The percentage of repair without a membrane, i.e. 'control', was 31.3±4.1% of the defect area of the middle section. Essential improvement of bone healing as compared with the control was achieved with OsseoQuest (55.78±9.9%), and E1M-11 NMP (77.6±8.8%). A direct comparison of bone healing enhanced by OsseoQuest and E1M-11 NMP shows a clearly better healing with E1M-11 NMP. Furthermore, E1M-3NMP shows a healing effect essentially similar to OsseoQuest.

As shown in FIG. 2 the membranes of the present invention, i.e. E1M-3 NMP and E1M-11 NMP, increase markedly the healing response in the defect as compared with the membranes with an identical polymeric composition, i.e. E1M-3, E1M-11, that do not comprise NMP.

EXAMPLE 3

According to one embodiment of the method of the present invention, NMP is added to the polymer matrix that has been already fashioned into the form of a medical implant.

Polymer compositions were prepared by dry-mixing commercially available granular-form base materials with commercially available copolymer additives. The material composition was 80 wt-% P(L/DL)LA (70/30) and 20 wt-% PLLA/TMC (70/30). The components were weighed according to a desired weight ratio into a container which was then rotated in a Turbula T2F shaker mixer for 30 minutes until a homogenous dry mixture was obtained. The resulting mixture was then dried in vacuum at 60° C. for 8 to 12 hours and thereafter melt-blended and injection-moulded in to plate-shaped test pieces. The injection-moulding machine used was a fully electric Fanuc Roboshot Alpha i30A injection-moulding machine with a mould clamping force of 300 kN. The injection unit was equipped with high speed (max. 66 cm$^3$/s to 330 mm/s), high pressure (max. 2500 bar) injection options. The barrel diameter was 16 mm and it was equipped with three-band heater zones, a standard profile anticorrosion screw and a standard open nozzle with a 2.5 mm hole. The extruder melt-blending and homogenization conditions of the material during the metering phase of the process included a back pressure of 40 to 60 bar, a screw speed of 60 to 100 rpm and barrel temperatures of 160 to 230° C. Injection moulding conditions included a nozzle temperature of 180 to 230° C., an injection speed of 80 to 300 mm/s, a maximum injection pressure of 2500 bar, a pack pressure of 1000 to 2300 bar for 3 to 8 s, a cooling time of 10 to 22 s and a mould temperature of 20 to 30° C. The total cycle time was 20 to 40 s consisting of the following phases during one injection-moulding process cycle: closing of the mould, injection of the molten polymer into the mould, pack pressure, cooling while extruder was metering for the next cycle during cooling phase, opening the mould and ejection of article from the mould.

The plates were sterilized by gamma irradiation with a nominal dose of 25 kGy. After sterilisation, the plates were submerged in NMP (1-Methyl-2-pyrrolidinone, 99%, Acros Organics, Inc., USA) for 30 seconds. After submerging the plates were set for 30 minutes on a plastic holder at room conditions at 20° C. Thickness, length and mass of the plates were measured before submerging and 30 minutes thereafter. Dimensions were measured with a slide gauge and mass with an analysis balance. Additionally, 30, 60 and 120 minutes after the submerging of the plate, it was bent to 45° angle to find out softening and bending characteristics of the plate. The diffusion depth of the NMP was analysed with SmartScope Flash optical 3D-measuring device. Approximately 1 mm of the material was cut off from the edge of the plate. The depth of the diffusion was measured from the cut cross-section of the plate 120 minutes after submerging. The results of the NMP diffusion after 30 min of submerging are shown in table 3.

TABLE 3

Mass and dimensions of the plate before and after submerging in the NMP

|  | Mass of the plate (mg) | Mass of the NMP in the plate (mg) | Thickness (mm) | Thickness of the outer layer (mm) | Length (mm) |
| --- | --- | --- | --- | --- | --- |
| Initial | 470.8 | — | 1.01 | 0 | 23.5 |
| 30 min after submerging | 575.7 | 104.9 | 1.15 | 0.15 | 23.6 |

The thickness of the plate was increased 13% and its mass was increased 22% due to the submerging of the plate in NMP. The increase of the mass can be seen as the diffusion of NMP into the plate. The increase of the thickness is due to the swelling of the outer layer of the plate. The thickness of the swollen outer layer of the plate was ca. 0.15 mm. The length was not changed due to the submerging. Moreover, 30 minutes after submerging the plate was softened and bendable by hand.

Resorbable polymer matrix absorbs NMP when immersed into it. Thereafter, an implant loaded with NMP is implanted into the body, and NMP is released gradually during a certain period of time. If the rate of releasing is appropriate, NMP owns osteogenic properties. As with almost any pharmaceuticals, the concentration of NMP must be within certain limits, called a therapeutic window. Below the window, NMP is inefficacious. Correspondingly, above the window, NMP presents an adverse event by inhibiting certain proteins, other molecules or cell lines. The NMP content is preferably between 0.05 and 50 weight-%, more preferably between 0.1 and 10 weight-%.

According to one preferred embodiment of the method of the present invention, NMP is mixed with a polymer matrix or one of its components before the polymer matrix is fashioned into the form of a medical implant. The mixing can take place in an extruder, in a mixer or similar equipment known per se.

NMP may be applied to the implant as well by packing said implant into a container with NMP already in the production process. NMP will be absorbed to the polymer matrix of the implant during storage in said container.

The polymer composition of the present invention can be fashioned into implants by injection moulding, compression moulding, extrusion or with another melt-moulding process known by persons skilled in the art.

EXAMPLE 4

Example 4 presents one preferred embodiment of the present invention, where the implant is a barrier membrane in Guided Tissue Regeneration (GTR) to treat a periodontal defect.

The membrane comprises PLA/PGA-matrix polymers. The membrane is packaged in a slot of a package, such as a plastic blister. The preparation of the membrane is conducted as one stage of surgical operation as follows:

1. After opening the package, a proper amount of NMP is poured into the membrane slot. The membrane is fully immersed in NMP for an adequate period, for example 30 seconds to 3 minutes, preferably for 30 seconds.
2. The membrane is removed from the slot.
3. NMP is allowed to diffuse into the polymer matrix of the membrane for 15 to 20 minutes.
4. The membrane is ready for use as a barrier between the gingival soft tissue and the healing bone tissue and/or periodontal tissues in order to prevent the gingival soft tissue filling the defect side. In the conditions of a normal operating theater temperature and humidity, the membrane stays malleable for several hours.

Implants of the invention can be used for example in guided bone regeneration applications, where the effect of a NMP loaded barrier membrane is required to avoid soft tissue ingrowth in the area where new bone formation is required, and to enhance bone regeneration.

It will be obvious to a person skilled in the art that, as the technology advances, the inventive concept can be implemented in various ways. The invention and its embodiments are not limited to the examples described above but may vary within the scope of the claims.

What is claimed is:

1. A resorbable polymer composition comprising:
a melt processed base material including a polymer matrix of resorbable polymer(s) or copolymer(s), and
N-methyl-2-pyrrolidone (NMP),
wherein the NMP is present in an amount imparting osteogenic properties to the resorbable polymer composition, and wherein the NMP is present in an amount between 0.05 and 50 weight-%.

2. A resorbable implant having osteogenic properties, comprising:
a melt processed base material including polymer matrix of resorbable polymer(s) or copolymer(s), and
wherein the NMP is present in an amount between 0.05 and 50 weight-%.

3. A method of making an implant having osteogenic properties comprising the steps of:
selecting polymer(s) or copolymer(s),
adding NMP to the polymer(s) or copolymer(s) in an amount imparting osteogenic properties to the implant,
melt processing the polymer(s) or copolymer(s) to form a polymer matrix, and
forming the implant from said polymer matrix.

4. A resorbable polymer composition comprising:
a melt processed base material including a polymer matrix of resorbable polymer(s) or copolymer(s), and
wherein the NMP is present in an amount between 0.05 and 50 weight-%.

5. The resorbable polymer composition of claim 4, wherein the polymer matrix is selected from a group consisting of polyglycolide, polylactides, polycaprolactones, polytrimethylenecarbonates, polyhydroxybutyrates, polyhydroxyvalerates polydioxanones, polyorthoesters, polycarbonates, polytyrosinecarbonates, polyorthocarbonates polyalkylene oxalates, polyalkylene succinates, poly (malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly (amino acids), modified polysaccharides, modified proteins and their copolymers, terpolymers or combinations or mixtures or polymer blends thereof.

6. The resorbable polymer composition of claim 4, wherein the polymer matrix is selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate) poly(D,L-lactide-co-trimethylenecarbonate), polydioxanone and their copolymers, terpolymers or combinations or mixtures or polymer blends thereof.

7. A resorbable implant, comprising:
a melt processed base material including polymer matrix of resorbable polymer(s) or copolymer(s), and
NMP, wherein the NMP is present in an amount between 0.05 and 50 weight-%.

8. The resorbable implant of claim 7, wherein the polymer matrix is selected from a group consisting of polyglycolide, polylactides, polycaprotactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof.

9. The resorbable implant of claim 7, wherein the polymer matrix is selected from a group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylencarbonate), poly(D,L-lactide-co-trimethylenecarbonate), polydioxanone and their copolymers, terpolymers or combinations or mixtures or polymer blends thereof.

10. A method of making an implant having osteogenic properties comprising the steps of:
selecting polymer(s) or copolymer(s),
adding NMP to the polymer(s) or copolymer(s) in an amount between 0.05 and 50 weight-%,
melt processing the polymer(s) or copolymer(s) to form a polymer matrix, and
forming the implant from said polymer matrix.

11. A method of making an implant having osteogenic properties comprising the steps of:
selecting polymer(s) or copolymer(s),
mixing said polymer(s) or copolymer(s),
melt processing the polymer(s) or copolymer(s) to form a polymer matrix,
forming the implant from said polymer matrix, and
adding NMP to the implant, wherein the NMP is present in an amount between 0.05 and 50 weight-%.

12. The method of making an implant having osteogenic properties of claim 11, wherein NMP is added to the implant preoperatively.

13. A method of promoting osteogenesis comprising the steps of:
providing a resorbable polymer composition comprising a melt processed base material including a polymer matrix of resorbable polymer(s) or copolymer(s) and NMP, wherein the NMP is present in an amount imparting osteogenic properties to the resorbable polymer composition, and wherein the NMP is present in an amount between 0.05 and 50 weight-%, and
implanting the resorbable polymer composition into a recipient to promote osteogenesis.

14. A method of promoting osteogensis comprising the steps of:
providing a resorbable implant comprising a melt processed base material including polymer matrix of resorbable polymer(s) or copolymer(s) and NMP, wherein the NMP is present in an amount between 0.05 and 50 weight-%, and
implanting the resorbable implant into a recipient to promote osteogenesis.

15. A method of promoting osteogenesis comprising the steps of:
selecting polymer(s) or copolymer(s),
adding NMP to the polymer(s) or copolymer(s) in an amount imparting osteogenic properties to the polymers(s) or copolymer(s), melt processing the polymer(s) or copolymer(s) to form a polymer matrix, forming an implant from the polymer matrix, and implanting the implant into a recipient to promote osteogenesis.

16. A method of promoting osteogenesis comprising the steps of:

providing a resorbable polymer composition comprising a melt processed base material including a polymer matrix of resorbable polymer(s) or copolymer(s) and NMP, wherein the NMP is present in an amount between 0.05 and 50 weight-%, and implanting the resorbable polymer composition into a recipient to promote osteogenesis.

17. The method of promoting osteogenesis of claim 16, wherein the polymer matrix is selected from a group consisting of polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof.

18. The method of promoting osteogenesis of claim 16, wherein the polymer matrix is selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and their copolymers, terpolymers or combinations or mixtures or polymer blends thereof.

19. The method of promoting osteogenesis of claim 14, wherein the polymer matrix is selected from a group consisting of polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof.

20. The method of promoting osteogenesis of claim 14, wherein the polymer matrix is selected from a group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and their copolymers, terpolymers or combinations or mixtures or polymer blends thereof.

21. A method of promoting osteogenesis comprising the steps of:

selecting polymer(s) or copolymer(s), adding NMP to the polymer(s) or copolymer(s) in an amount between 0.05 and 50 weight-%, melt processing the polymer(s) or copolymers to form a polymer matrix, forming an implant from said polymer matrix, and implanting the implant into a recipient to promote osteogenesis.

22. A method of promoting osteogenesis comprising the steps of:

selecting polymer(s) or copolymer(s), melting process said polymer(s) or copolymer(s) to form a polymer matrix, forming an implant from said polymer matrix, adding NMP to the implant, wherein the NMP is present in an amount between 0.05 and 50 weight-%, and implanting the implant into a recipient to promote osteogenesis.

23. The method of promoting osteogenesis of claim 22, wherein the NMP is added to the implant preoperatively.

* * * * *